United States Patent
Fiala et al.

(10) Patent No.: US 8,465,543 B2
(45) Date of Patent: Jun. 18, 2013

(54) ASTIGMATIC INTRAOCULAR LENS

(75) Inventors: Werner Fiala, Vienna (AT); Christine Kreiner, Munich (DE)

(73) Assignee: Carl Zeiss Meditec AG, Jena (DE)

(*) Notice: Subject to any disclaimer, the term of this patent is extended or adjusted under 35 U.S.C. 154(b) by 305 days.

(21) Appl. No.: 11/916,635

(22) PCT Filed: Jun. 22, 2006

(86) PCT No.: PCT/EP2006/006041
§ 371 (c)(1),
(2), (4) Date: Dec. 15, 2008

(87) PCT Pub. No.: WO2006/136424
PCT Pub. Date: Dec. 28, 2006

(65) Prior Publication Data
US 2009/0132041 A1    May 21, 2009

(30) Foreign Application Priority Data
Jun. 22, 2005   (DE) .................. 10 2005 028 933

(51) Int. Cl.
*A61F 2/16* (2006.01)
(52) U.S. Cl.
USPC ........................... 623/6.23; 623/6.24
(58) Field of Classification Search
USPC .............................. 623/6.23, 6.24
See application file for complete search history.

(56) References Cited

U.S. PATENT DOCUMENTS

| 5,173,723 | A | * | 12/1992 | Volk ........................... 351/161 |
| 5,796,462 | A | * | 8/1998 | Roffman et al. ............. 623/6.24 |
| 5,800,532 | A | | 9/1998 | Lieberman ................... 623/6 |
| 6,142,625 | A | * | 11/2000 | Sawano et al. ............... 351/161 |
| 2003/0014107 | A1 | | 1/2003 | Reynard ....................... 623/6.24 |
| 2003/0060880 | A1 | | 3/2003 | Feingold ...................... 623/6.27 |
| 2003/0086055 | A1 | * | 5/2003 | Morris et al. ................ 351/159 |
| 2006/0116763 | A1 | * | 6/2006 | Simpson ...................... 623/6.23 |
| 2006/0167545 | A1 | | 7/2006 | Fiala et al. |

FOREIGN PATENT DOCUMENTS

| CN | 1164652 A | 11/1997 |
| EP | 0 742 461 A2 | 11/1996 |
| EP | 0 949 529 A2 | 10/1999 |
| WO | 03/009053 A1 | 1/2003 |
| WO | 2004/090611 A2 | 10/2004 |

* cited by examiner

*Primary Examiner* — David H Willse
*Assistant Examiner* — Tiffany Shipmon
(74) *Attorney, Agent, or Firm* — Robert Iannucci; Seed IP Law Group PLLC (57) ABSTRACT

The invention concerns an intraocular lens for the correction of astigmatic ametropia, which has both a torically refractive front face and a torically refractive rear face. The intraocular lens also has a torically refractive lens surface whose section curve in at least one principal meridian is described by an asphere. Finally the intraocular lens has a torically refractive lens surface with two principal meridians which include an intermediate angle that is not equal to 90°.

7 Claims, 4 Drawing Sheets

Angle between meridian 14 and meridian 1 in Fig 4

Fig. 5

Fig. 6a (front face)    Fig. 6b (rear face)

Fig. 7

ASTIGMATIC INTRAOCULAR LENS

The present invention concerns an intraocular lens (IOL) for the correction of astigmatic ametropia.

BACKGROUND OF THE INVENTION

Lenses serve generally for converting a light wave into another light wave. An essential function of lens optics is to convert a spherical light wave from an object point in such a way that the resulting wave is also spherical and thus the image point which is in conjugate relationship with the object point is the centre of the resulting spherical wave fronts. A wave incident from an object point is always spherical; if the object point is disposed at (practically) infinite distance, the incident wave is flat or plane. Hereinafter incident plane waves are also embraced by the generic term 'incident spherical wave'.

Lens systems for producing the image of an object point at a conjugate image point can include lenses or refractive surfaces which do not involve rotational symmetry. An incident spherical wave is converted by such lenses or surfaces into a wave, the wave fronts of which do not involve rotational symmetry; the wave fronts are 'distorted'. Such wave fronts are then converted by means of so-called 'astigmatic' lenses or refractive surfaces which in turn do not involve any rotational symmetry, into waves whose wave fronts in turn involve rotational symmetry.

A known example of a refractive surface which converts an incident spherical wave into a wave, the wave fronts of which do not involve rotational symmetry, is the surface of an astigmatic cornea or an astigmatic lens of the eye. The distorted wave fronts are then to be converted in the pseudophakic eye by astigmatic lenses into wave fronts involving rotational symmetry, generally into spherical waves. To correct the astigmatism of the cornea or the eye which is essentially to be attributed to a non-spherically (for example torically) shaped cornea and/or other abnormalities of the eye such as for example an eye lens without rotational symmetry or a retinal abnormality, contact lenses, intraocular lenses and also spectacles lenses are used. In the present case only intraocular lenses are being considered.

Known intraocular lenses for the correction of astigmatic ametropia have a cylindrically or torically refractive boundary face and a (spherically or aspherically) rotationally symmetrically refractive boundary face.

A torically refractive or toric face is afforded by rotation of a circular arc segment or a circle about an axis which does not include the centre point of the circle. If the greatest distance between the circle and the axis of rotation is smaller than the radius of the circle the resulting toric face is referred to as 'barrel-shaped', while if that distance is greater than the radius of the circle, that involves a 'sausage-shaped' toric face (according to the 'Handbuch für Augenoptik', editor, Carl Zeiss, page 23 (1977)). In linguistic usage 'toric' and 'astigmatic' are frequently used synonymously. Hereinafter the term 'toric' is used throughout, even if the lens surface described in that way is not toric in the mathematical sense.

The toric lens surface provides that the refractive power of the IOL in one meridian is different from the refractive power in the other meridian. The two meridians are perpendicular to each other. The difference in the two refractive powers is usually referred to as the lens cylinder as the optical effect of such a toric IOL corresponds to that of a combination of a spherical lens and a cylindrical lens. A cylindrical lens has the refractive power zero for the plane of incidence of the light, which contains the axis of the cylinder, and, in the plane perpendicular to that plane of incidence, it involves the maximum refractive power which is given substantially by the radius of the cylinder and the refractive index of the cylindrical lens. That maximum refractive power of the cylindrical lens is therefore briefly referred to as 'lens cylinder' (in dioptres). It will be clear from the foregoing that the two meridians of a toric lens in which the lens refractive power is on the one hand of the maximum value and on the other hand of the minimum value—what are referred to as the principal meridians—are perpendicular to each other and the difference of the maximum refractive power and the minimum refractive power is the lens cylinder of the toric lens.

In other words the toric face involves different radii of curvature in the principal meridians. In each plane which is perpendicular to the lens axis the section line of the (spherically or aspherically) rotationally symmetrically refractive boundary face is a circle and the section line of the toric face is an ellipse. The minor axis of that ellipse is determined by the shorter radius in the associated principal meridian while the major axis of the ellipse is determined by the larger radius of curvature in the other principal meridian. By virtue of the elliptical shape, in the case of the toric face being delimited by a plane, the optically effective face for the greater of the two refractive powers of the lens is smaller than for the lower of the two refractive powers.

Figure 1A:
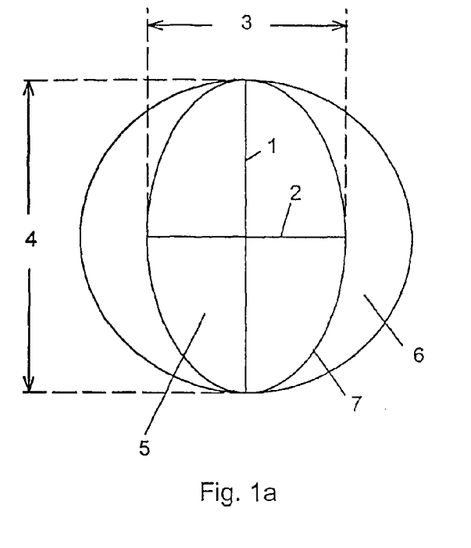
FIG. 1 shows a diagrammatic projection of the toric face of a toric IOL in accordance with the state of the art.
Figure 1B:
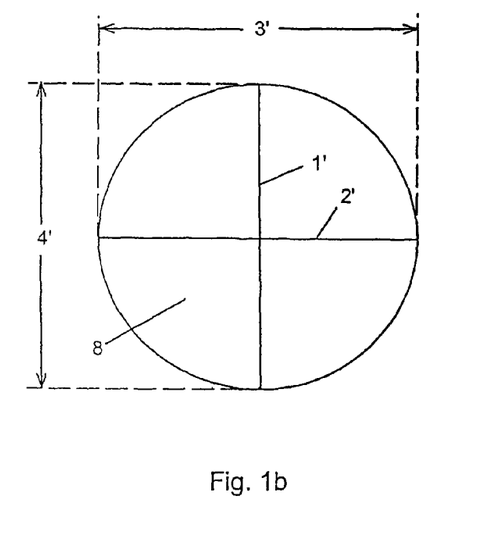

FIG. 1a diagrammatically shows the projection of the toric face of a conventional toric IOL. In this Figure, reference 1 is the meridian with the lower of the two refractive powers while reference 2 is the meridian of the greater of the two refractive powers. The radius R1 in the meridian 1 is larger than the radius R2 in the meridian 2, that is to say R1>R2. The ellipse 7, projected on to a flat surface 6, of the toric refractive face 5 has the minor axis 3 and the major axis 4. The optically effective face is limited to the inner region of the ellipse as shown in FIG. 1a, The projection of the other, namely spherical, refractive face 8 of the conventional toric lens is shown in FIG. 1b. The section line of that refractive face with a plane is a circle, the 'axis lengths' 3' and 4' of which, along the two meridians 1' and 2', are trivially the same.

Figure 2:
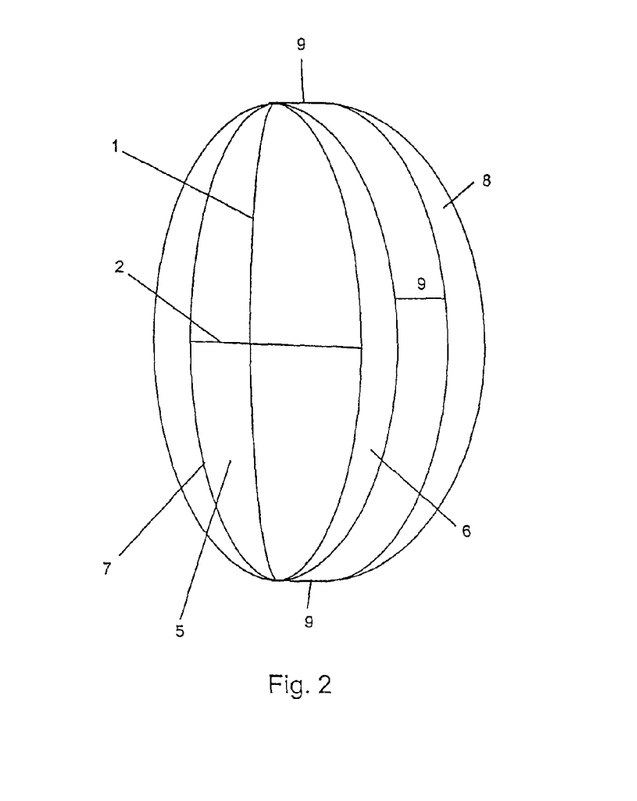
FIG. 2 shows a diagrammatic perspective view of the known IOL shown in FIG. 1.

FIG. 2 shows a diagrammatic perspective view of such a lens with an edge thickness 9 which is constant over the entire periphery.

Thus, with a given constant edge thickness, conventional toric lenses generally have an optically effective face which is reduced to the area of an ellipse.

In addition conventional toric lenses have two refractive faces, the one face being spherical and the other face being toric; the section lines in the principal meridians of the toric lens surface are determined by equations of a circle, by virtue of their rotational symmetry, with the principal meridians being arranged in mutually orthogonal relationship, as described hereinbefore. However such lenses are suitable only in rare cases for the conversion of wave fronts which occur due to refraction at astigmatic refractive faces like the cornea, into spherical waves.

The object of the invention is to improve the optically effective face of a toric (or astigmatic) IOL and to improve the correction properties in the case of astigmatic ametropia.

Subject-Matter of the Invention

According to the invention in an IOL of the kind set forth in the opening part of this specification that object is attained in that the intraocular lens has both a torically refractive front face and a torically refractive rear face.

As is described in greater detail hereinafter that increases the size of the optically effective face of the IOL. Preferably in that case the front face and the rear face are of a convex shape. In the rare cases of a negative lens both faces are concave. At any event however it is advantageous if the front face and the rear face involve the same direction of curvature and thus the refraction thereof involve the same sign. Particularly preferably the cylindrical effect is approximately uniformly distributed to the front face and the rear face. With identical distribution—that is to say an identical toric surface on the front side and the rear side of the IOL—the optically effective face is at its greatest. It will be appreciated that unequal distributions of toricity are also covered by the subject-matter of the invention, in which optimisation of the size of the optically effective face is of less significance in relation to other imaging properties.

In accordance with the invention the aims in the case of an IOL of the kind set forth in the opening part of this specification are further achieved in that the intraocular lens has a torically refractive lens surface whose section curve of a plane parallel to the lens axis, in a principal meridian, is described by an asphere. In that case the oppositely disposed lens surface is also toric, rotationally symmetrically spherical or rotationally symmetrically aspherical.

Preferably the section curves of the torically refractive lens surface with respect to the lens axis of parallel planes, in both principal meridians, are each described by an asphere.

Surfaces whose section curve are aspherical in a principal meridian are herein also referred to as toric lens surfaces. Such surfaces are produced by rotation of curves which are not in the form of a circular arc for, in the case of toric faces which are always produced by the rotation of a curve, at least one of the two meridians is circular. Although faces which cannot be represented as the result of rotation of a curve, because the section curves are aspherical in both principal meridians and which therefore are not 'toric' faces in the truly mathematical sense, herein they are also embraced by toric. The section lines of the planes parallel to the lens axis in the principal meridians of such astigmatic faces are determined by equations which apply to aspherical curves. This aspect will be discussed in greater detail hereinafter.

If the toric surface of the IOL is not limited to that which can be generated by the rotation of a circular arc, the imaging property of the IOL according to the invention can be better adapted to the specific form of the wave front produced by refraction of an incident spherical wave at an astigmatic face of the eye or lens.

In accordance with the invention, in an IOL of the kind set forth in the opening part of this specification, the aims are further achieved in that the intraocular lens has a torically refractive lens surface with two principal meridians which include an intermediate angle that is not equal to 90°. In that case the oppositely disposed lens surface can again also be toric, rotationally symmetrical spherical or rotationally symmetrical aspherical.

Refractive faces in respect of which the meridian with the greatest refractive power includes an angle that is not equal to 90° with the meridian with the lowest refractive power are again strictly mathematically not referred to as 'toric' faces, but nonetheless they are embraced by that term herein.

An angle between the planes through the principal meridians, which is not restricted to the value of 90°, also serves to better adapt the imaging properties of the IOL according to the invention, to the specific form of the wave front produced by refraction of the incident spherical wave at an astigmatic face of the eye or lens.

In an advantageous embodiment the invention also provides that the intraocular lens combines the features of a torically refractive front face and a torically refractive rear face with those of at least a torically refractive lens surface whose section curve or curves of a plane or two planes parallel to the lens axis, in one or both principle meridians respectively, are described by aspheres.

In a further advantageous embodiment the invention also provides that the intraocular lens combines the features of a torically refractive front face and a torically refractive rear face with those of a torically refractive lens surface of which two principal meridians include an intermediate angle that is not equal to 90°.

In an advantageous embodiment the invention further provides that the intraocular lens combines the features of a torically refractive lens surface whose section curve or curves of a plane or two planes parallel to the lens axis in one or both principal meridians respectively are described by aspheres, with those of a torically refractive lens surface whose two meridians include an intermediate angle that is not equal to 90°.

Finally in a further advantageous embodiment the invention provides that the intraocular lens combines the features of a torically refractive front face and a torically refractive rear face with those of at least a torically refractive lens surface whose section curve or curves of a plane or two planes parallel to the lens axis in one or both principal meridians respectively are described by aspheres, and those of a torically refractive lens surface of which two principal meridians include an intermediate angle that is not equal to 90°.

The toric IOL according to the invention (or actually the IOL for the correction of astigmatic ametropia) can be adjusted by means of the specified features with a much higher degree of precision to the individual ametropia due to an astigmatic face of the eye to be treated so that it converts wave fronts which are formed by the refraction of light at that non-spherical astigmatic face (cornea, lens of the eye etc), into substantially spherical wave fronts. In other words the IOL according to the invention provides that the beams which emanate from an object point and which are refracted by astigmatic refractive faces (cornea, lens of the eye etc) are refracted in such a way that that object point is imaged substantially at precisely one image point. Imaging of the overall system comprising the astigmatic refractive face of the eye and the IOL according to the invention is stigmatic. At this juncture it is noted that the IOL according to the invention includes both so-called 'phakic' and also so-called 'pseudophakic' intraocular lenses, that is to say both those which are implanted in place of the natural lens of the eye and also in addition thereto.

Further features and advantages of the IOL according to the invention are set forth in the appendant claims. They are described with reference to the accompanying Figures in the description hereinafter. In the Figures:

FIG. 3 shows a diagrammatic projection of the lens front face (FIG. 3a) and the lens rear face (FIG. 3b) of an embodiment of the IOL according to the invention on to a plane, FIG. 6 shows an elevational view of the front face FIG. 6a and the elevational view of the associated rear face FIG. 6b of the toric face of an embodiment of the IOL according to the invention, in which the principal meridian with the lowest refractive power includes an angle χ that is not equal to 90°, with the principal meridian having the highest refractive power.

If, in a toric lens, a toric face, for example the front face, is combined with a spherical face, for example the rear face, the projection of that toric (front) face on to a plane is an ellipse having the axes 1 and 2 shown in FIG. 1*a*. The length of the major axis 1 of the ellipse is to be identified by $a_m$ while the length of the minor axis 2 is to be identified by $b_m$. In addition, the radius of curvature of the toric face in the principal meridian 1 is identified by $R1_m$ and the radius of curvature in the principal meridian 2 is identified by $R2_m$. The radius of the spherical (rear) face of the toric lens is to be identified by $R_s$. The refractive power D1 in the principal meridian 1 of the lens is then given by:

$$D1 = \frac{n_L - n_{imm}}{R1_m} + \frac{n_L - n_{imm}}{R_S} - \frac{t(n_L - n_{imm})^2}{n_L R1_m R_S} \quad (1)$$

wherein:
$n_L$ ... index of the lens
$n_{imm}$ ... index of the medium surrounding the lens
t ... centre thickness of the lens.

In equation (1) radii are of a positive value if they are convex for light which is or would be incident on the lens face being considered, from the exterior. In the case of a biconvex lens therefore both $R1_m$ and also $R_S$ are positive.

In the same manner the refractive power D2 in the principal meridian 2 of the lens is given by:

$$D2 = \frac{n_L - n_{imm}}{R2_m} + \frac{n_L - n_{imm}}{R_S} - \frac{t(n_L - n_{imm})^2}{n_L R2_m R_S} \quad (2)$$

The cylinder Z of the toric lens is given in a very good approximation by:

$$Z = D2 - D1 \approx \frac{n_L - n_{imm}}{R2_m} - \frac{n_L - n_{imm}}{R1_m} \quad (3)$$

as the difference in the two third terms of equations (1) and (2) is extremely slight. As the third terms (which only represent a correction factor for the centre thickness of the lens) in equations (1) and (2) are small in relation to the other terms, they are not taken into consideration in the considerations in principle set out hereinafter.

If in comparison a lens according to the invention is designed in such a way that both the front face and also the rear face are toric, then with the same cylindrical action in respect of the lens the lengths $b_b$ of the axes of the ellipse of the two toric faces are greater than $b_m$, that is to say the effective optical face is greater in comparison with a conventional toric lens with only one toric and one spherical refractive face. As an example it may be assumed that the cylindrical action of the lens is distributed in equal parts to the front face and the rear face. Then each of those faces must involve the cylinder Z/2. The radius in the principal meridian with the lower refractive power is to be $R1_b$, and without limitation in terms of generality it will be assumed that $R1_b = R1_m$. Then the radius $R2_b$ in the principal meridian with the greater refractive power is determined to a very good approximation by the following equation:

$$\frac{Z}{2} \approx \frac{n_L - n_{imm}}{R2_b} - \frac{n_L - n_{imm}}{R1_m} \quad (4)$$

Combining equations (3) and (4) and resolving them in accordance with $R2_b$ gives:

$$R2_b = \frac{2R1_m R2_m}{R1_m + R2_m} > R2_m \quad (5)$$

as $R2_m < R1_m$.

Figure 3A:
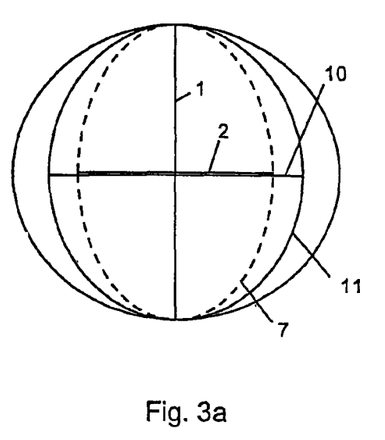
Figure 3B:
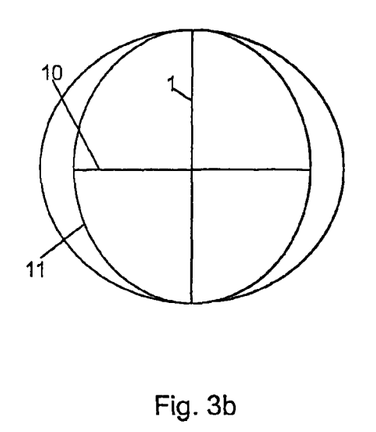

The circumstances are diagrammatically shown in FIGS. 3*a* and 3*b*. In this case FIG. 3*a* is the projection of the lens front face on to a plane and FIG. 3*b* is the projection of the rear face of the lens according to the invention on to a plane. In this Figure reference 1 is the principal meridian involving the lower refractive power, reference 2 is the principal meridian of the greater refractive power of a toric lens, which as the second refractive face has a spherical face, and reference 10 is the principal meridian of a toric lens which has two similar faces which are torically refractive in mirror-identical fashion; both lenses have the same cylinder. The major axis of the ellipse in the principal meridian 1 of the lower refractive power is $a_m$ in the case of the lens with only one torically refractive face and $a_b$ in the case of the lens with two toric faces. That ellipse axis is here identical in both cases, that is to say $a_b = a_m$. The minor axis of the ellipse in the principal meridian 2 of the greater refractive power of the lens with only one toric face is $b_m$, while the minor axis of the ellipse in the principal meridian 10 with the greater refractive power of the lens with two toric faces is $b_b$. It will be apparent that the effective optical area of the lens with two toric faces is greater than that with only one toric face and one spherical face.

Distribution of the cylinder in equal parts to the front and rear faces of a lens according to the invention is arbitrary; it will be appreciated that it is also possible for that cylinder to be distributed in different ways.

The results for lenses with the lower refractive power of 10 dioptres and a cylinder of +6 dioptres will be set forth to illustrate the situation. It will be assumed that the lens is made from a material with a refractive index $n_L = 1.49$ and is in a medium with a refractive index $n_{imm} = 1.336$. The major axis of the ellipse (for the lower refractive power of 10 dioptres) is assumed to be 10 mm. Then, for the minor axis of the ellipse for a lens with only one toric and one spherical refractive surface, that gives the value of 6.03 mm; for the minor axis of the ellipse of the lens with two toric faces of mirror-symmetrical configuration that gives the value of 7.9 mm.

The foregoing considerations apply for toric lenses whose section curves in the principal meridians are given as a special case by equations of a circle.

For the conversion of wave fronts which are produced by refraction of a plane wave at an astigmatic or toric face into spherical waves, astigmatic lenses may be required, whose section curves in the principal meridians are given by asphere equations. In accordance with the invention therefore astigmatic lenses have in the principal meridians curves which are given by asphere equations. In such lenses according to the invention the equations of the curves in the principal meridians of the refractive face or faces are given by the apex equations of aspheres. The form of such equations is as follows:

$$y = \sqrt{2Rx - (1 + asp)x^2} \quad (6)$$

wherein

R ... radius or parameter at the apex of the lens asp ... asphericity of the asphere.

The radius R is correspondingly given by $R1_m$ or $R2_m$ or $R1_b$ or $R2_b$ as, for light beams near the axis, that is to say within the region of Gaussian optics, the refractive laws on lenses for spherical and aspherical faces of the same radius or parameter are practically identical.

The asphericities in the two principal meridians can be different. If asp1 is used to identify the asphericity in the principal meridian 1 and asp2 is used to identify the asphericity in the principal meridian 2, then either one of the following applies:

$$asp1 = asp2 \quad (7)$$

or $$asp1 \neq asp2 \quad (7')$$

The values for the appropriate values for asp1 and asp2 depend on the form of the wave which is produced by refraction of a plane wave at an astigmatic refractive face.

For certain situations of use it may be necessary to provide in the principal meridians section curves with the refractive face of lenses according to the invention, which cannot be represented by the apex equation of a simple asphere in accordance with equation (6), that is to say by the equation of a conic section. It is then appropriate to adopt a different form of representation for that section curve, which is obtained by resolving the equation (6) and by the addition of a power series:

$$x = \frac{y^2/R}{1 + \sqrt{1-(1+asp)y^2/R^2}} + \sum_j c_j y^j \quad (8)$$

wherein $c_j$ are polynomial coefficients.

If a form of representation of the asphere in accordance with equation (8) is selected, the values for the coefficients $c_j$ are to be determined in each of the principal meridians, besides asphericity; in general, because of the usual monotony of the curve in accordance with equation (8) only even-numbered terms in equation (8) are taken into consideration.

The general considerations which apply for lenses according to the invention with asphere equations in the section curves of the principal meridians of the refractive face or faces in accordance with equation (7) also apply mutatis mutandis for lenses according to the invention with asphere equations in the corresponding section curves in accordance with equation (8).

In general the choice of the various parameters R and asp in the meridians of the one or both toric or astigmatic faces or the spherical face of a toric lens depends on the incident wave which is to be converted into a spherical wave by that lens. The operation of determining the values for the two radii or parameters and the two asphericities in the principal meridians 20 of the lens can be effected by computer-supported iterative methods in which all light beams being considered are refracted at the existing faces. Such methods require the analytical three-dimensional representation of all refractive faces in the lens system, calculation of the normal vectors in any positions on those faces (gradient formation) and the three-dimensional 25 refraction law in vector form. Such methods are readily understandable for the man skilled in the art; they do not represent subject-matter of the present invention. Furthermore general guidelines for the suitable selection of those parameters can be found in U.S. Application Publication No. 2006/0167545.

Thus a lens according to the invention has in the principal meridians of the refractive face or faces curves which analytically can be represented by the apex equations of aspheres in accordance with equation (6) or equation (8) respectively. In other words the section curves with axis-parallel planes in the principal meridians, in the case of the representation in accordance with equation (6), are aspheres with a parameter or radius R and an asphericity asp, and in the case of the representation in accordance with equation (8), additionally with the coefficients $c_j$.

Figure 4:
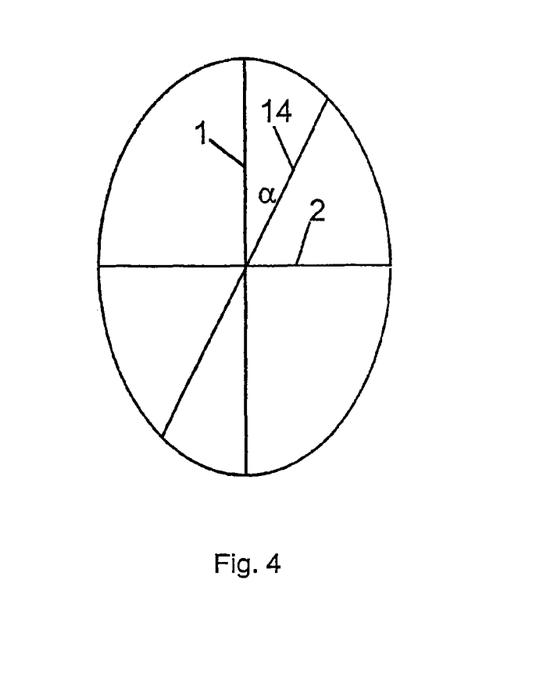
FIG. 4 shows a diagrammatic projection of the toric face of an embodiment of the IOL according to the invention, with an (intermediate) meridian of the function of an angle α.

The section curves of axis-parallel planes in the meridians between the principal meridians can be represented as a function of the parameters or radii and the asphericities in the principal meridians and the angle between the meridian being considered and one of the principal meridians. The circumstances are shown in FIG. 4. The principal meridian with the lowest refractive power is again identified by reference 1 and the principal meridian with the greatest refractive power is identified by reference 2. It is assumed that a meridian 14 forms an angle $\alpha$ with the principal meridian 1, and the radius or parameter in that meridian is identified by $R_\alpha$.

The following then generally applies for the radius or parameter $R_\alpha$:

$$R_\alpha = f(\alpha) \quad (9)$$

with the boundary conditions:

$$f(0) = f(180°) = R1$$

$$f(90°) = f(270°) = R2$$

$$f'(\alpha) < 0 \text{ for } 0 < \alpha < 90° \text{ and } 180° < \alpha < 270°$$

$$f'(\alpha) > 0 \text{ for } 90° < \alpha < 180° \text{ and } 270° < \alpha < 360° \quad (10)$$

in other words, because R1>R2 that function must be monotonically falling between 0° and 90° and 180° and 270° and monotonically rising between 90° and 180°, and 270° and 360°. It will be apparent that a large number of functions is available for selection for $f(\alpha)$. The most suitable function $f(\alpha)$ can be determined only with knowledge of the wave front incident on the lens, which is to be converted into a spherical wave front by the lens according to the invention. Various mathematical approaches for $f(\alpha)$ are generally to be tested to determine the optimum function $f(\alpha)$.

The following are to be mentioned purely as examples of valid approaches for the function $f(\alpha)$:

$$R_\alpha = f_1(\alpha) = R1 \times \cos^2\alpha + R2 \times \sin^2\alpha \quad (11)$$

or $$R_\alpha = f_2(\alpha) = \sqrt{R1^2 \times \cos^2\alpha + R2^2 \times \sin^2\alpha} \quad (12)$$

or $$R_\alpha = f_3(\alpha) = \frac{1}{\frac{1}{R1}\cos^2\alpha + \frac{1}{R2}\sin^2\alpha} \quad (13)$$

Figure 5:
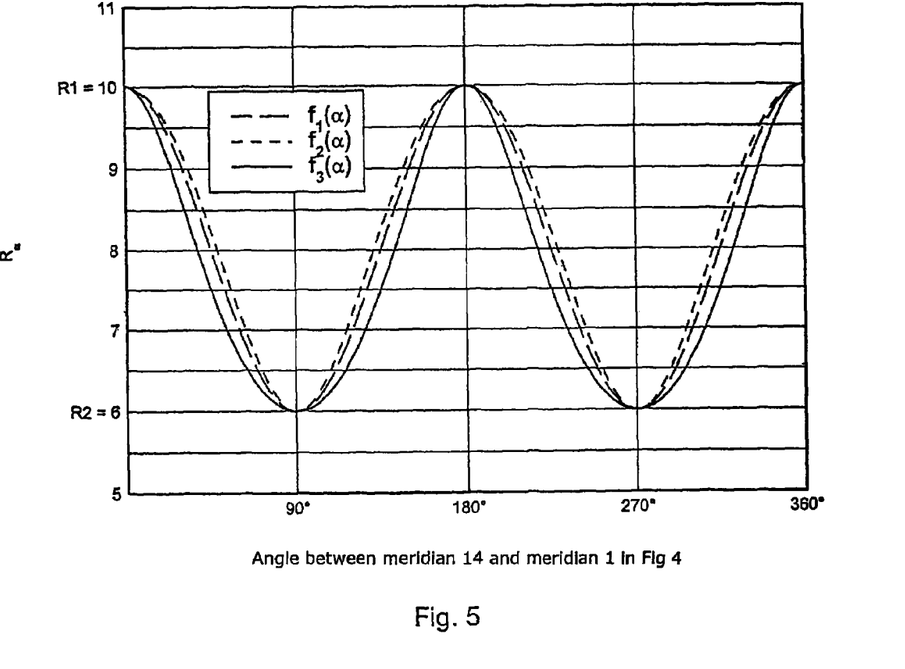
FIG. 5 shows a graph in which three functions for the radius of curvature of the toric face of the embodiment of FIG. 4 are plotted against the angle α.

FIG. 5 shows the above three functions for the values R1=10 and R2=6 by way of example for valid approaches in respect of $f(\alpha)$. Countless other forms of function for $f(\alpha)$ are possible.

The asphericities in the principal meridians 1 and 2 are mostly different but can also be the same. At any event the value for the asphericity $asp_\alpha$ in the meridian 14 can again be implemented as the function of the two asphericities asp1 and asp2 in the principal meridians and the angle $\alpha$. In that respect it is possible to use similar functions to the above-mentioned $f_i(\alpha)$ or other functions $g(\alpha)$.

If in general we identify the function for the parameter $R_\alpha$ with $f(\alpha, R1, R2)$ and the function for the asphericity $asp_\alpha$ of the astigmatic lens face with $g(\alpha, asp1, asp2)$, then the astigmatic face can be represented as follows (without higher-order terms):

$$y^2+z^2=2R_\alpha x-(1+asp_\alpha)x^2 \tag{14}$$

Equation (14) can also be represented as:

$$F(x,y,z)=x^2+y^2+z^2-2R_\alpha x+asp_\alpha x^2=0 \tag{14'}$$

wherein:

$$R_\alpha = f(\alpha, R1, R2)$$

and $$asp_\alpha = g(\alpha, asp1, asp2) \tag{15}$$

If the principal meridian is disposed in the xy-plane with the x-axis as the lens axis, then $\alpha$ can be represented as:

$$\alpha = \arctan(z/y) \tag{16}$$

and by inserting equation (16) into equation (14') that gives the representation of the astigmatic refractive face of a lens according to the invention in Cartesian co-ordinates.

As an example attention is directed to the equation of an astigmatic face in which both the parameter $R_\alpha$ and also the asphericity $asp_\alpha$ are represented by functions of the type $f_1(\alpha)$. Furthermore the direction of the principal meridian 1 is assumed to be the y-direction and the direction of the principal meridian 2 the z-direction. In other words:

$R1=R_{xy}$ and $asp1=asp_{xy}$ as well as
$R2=R_{xz}$ and $asp2=asp_{xz}$

That therefore gives the following expression for the astigmatic face of the lens according to the invention:

$$F(x,y,z)=x^2+y^2+z^2+\frac{y^2}{y^2+z^2}asp_{xy}x^2+ \tag{17}$$
$$\frac{z^2}{y^2+z^2}asp_{xz}x^2 - 2\frac{y^2}{y^2+z^2}R_{xy}x - 2\frac{z^2}{y^2+z^2}R_{xz}x$$
$$=0$$

Finally the situation is also to be considered where the principal meridians of an astigmatic refractive face are not in mutually orthogonal relationship.

Figure 6A:
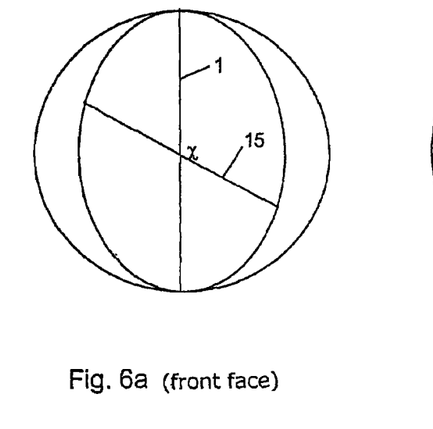
Figure 6B:
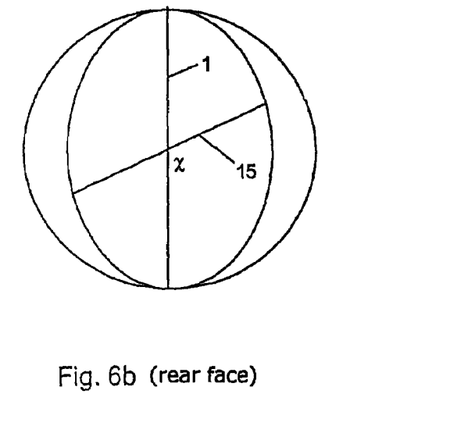

FIG. 6a shows the front view (elevational view) of the astigmatic face of an astigmatic lens while FIG. 6b shows the elevational view of the associated rear face of that astigmatic lens.

The angle between the principal meridians 1 and 15 (FIG. 6a and FIG. 6b respectively) is therefore given not by 90° but by an angle $\chi$. The parameters in the principal meridians are once again assumed to be R1 and asp1, and R2 and asp2 respectively. Then, for meridians between the non-orthogonal principal meridians, the parameters $R_\alpha$ and $asp_\alpha$ can be represented in a similar fashion, as shown above. It will be noted however that in equations (15) the angle argument $\alpha$ is to be replaced by $\alpha'$, wherein the connection between those values is given by the following relationships:

$$\alpha' = 90\frac{\alpha}{\chi} \quad \text{for } 0 \leq \alpha \leq \chi \tag{18}$$

$$\alpha' = 90\frac{180-2\chi+\alpha}{180-\chi} \quad \text{for } \chi \leq \alpha \leq 180$$

$$\alpha' = 180 + 90\frac{\alpha-180}{\chi} \quad \text{for } 180 \leq \alpha \leq 180+\chi$$

$$\alpha' = 180 + 90\frac{\alpha-2\chi}{180-\chi} \quad \text{for } 180+\chi \leq \alpha \leq 360$$

Figure 7:
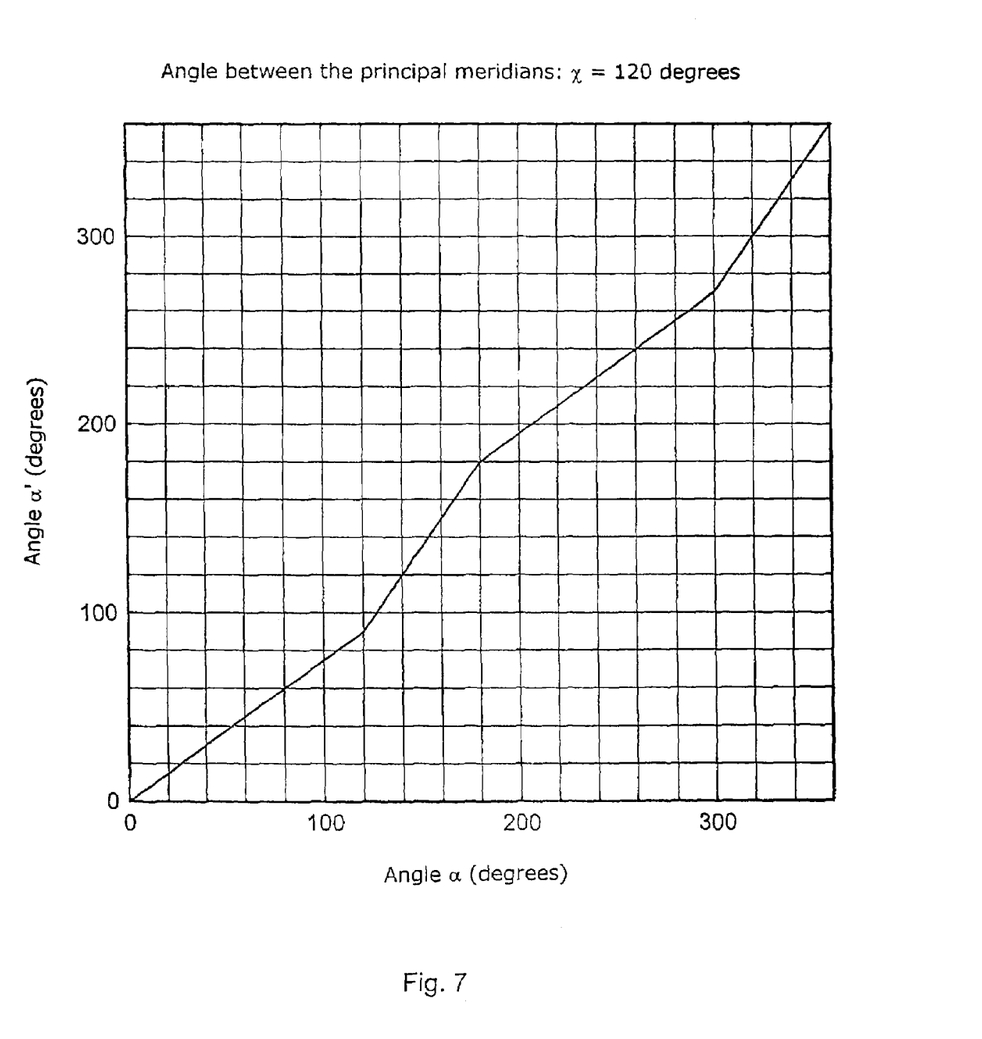

FIG. 7 shows the connection between $\alpha$ and $\alpha'$ for the case of an angle $\chi=120°$.

The connections in accordance with equation (18) are linear. It will be appreciated that the connection between $\alpha$ and $\alpha'$ can be produced by other, non-linear functions $\alpha'=h(\alpha)$. It will be noted however that rising monotony is to be required of the function $h(\alpha)$, with a rising value for $\alpha$. In addition $h(\alpha)$ must afford the value $\alpha'=90°$ for $\alpha=\chi$, or generally the values $\alpha'=0, 90, 180, 270$ and $360°$ for the angle $\alpha$, which coincide with the angles of the principal meridians $(0, \chi, 180°, 180°+\chi, 360°)$.

Lenses according to the invention with astigmatic refractive faces of the described kind are substantially better suitable for the conversion of wave fronts which are produced by refraction at non-rotationally symmetrical refractive faces into spherical wave fronts than conventional toric lenses with a toric and a spherical refractive face.

The invention claimed is:

1. An intraocular lens for the correction of an astigmatic ametropia comprising a torically refractive lens surface, wherein a total section curve in a principal meridian of the torically refractive lens surface in a plane parallel to a lens axis is described by an asphere according to an equation:

$$y=\sqrt{2Rx-(1+asp)x^2}$$

or $$x = \frac{y^2/R}{1+\sqrt{1-(1+asp)y^2/R^2}} + \sum_j c_j y^j$$

wherein
x is a first coordinate axis being in the direction of the lens axis,
y is a second coordinate axis being in the direction of a first principal meridian,
R is a radius or parameter at an apex of the lens,
asp is an asphericity in the meridian,
cj are polynomial coefficients,
wherein R is a value of a radius R1 of a curvature of the torically refractive lens surface in the first principal meridian and of a radius R2 of a curvature of the torically refractive lens surface in a second principal meridian, wherein R1 differs from R2,
wherein asp is a value of a first asphericity asp1 in the first principal meridian and of a second asphericity asp2 in the second principal meridian of the torically refractive lens surface, wherein asp1 is different from asp2,
wherein a meridian forming an angle $\alpha$ with the first principle meridian comprises an asphericity $asp\alpha$ which depends on the angle $\alpha$.

2. An intraocular lens according to claim 1 wherein the intraocular lens has both a torically refractive front face and also a torically refractive rear face.

3. An intraocular lens according to claim 2 wherein the front face and the rear face are of a convex shape.

4. An intraocular lens according to claim 1, wherein a cylindrical shape is substantially uniformly distributed to the front face and the rear face.

5. An intraocular lens according to claim 1, wherein section curves of the torically refractive lens surface in both principal meridians in planes parallel to the lens axis are respectively described by an asphere.

6. An intraocular lens according to claim 1, wherein said torically refractive lens surface has two principal meridians which include an intermediate angle that is not equal to 90°.

7. An intraocular lens according to claim 1 wherein a front face of the intraocular lens and a rear face of the intraocular lens have a convex shape.

\* \* \* \* \*